(12) United States Patent
Huang et al.

(10) Patent No.: US 8,741,201 B2
(45) Date of Patent: Jun. 3, 2014

(54) FIBER REINFORCED COMPOSITE STENTS

(75) Inventors: Bin Huang, Pleasanton, CA (US); David C. Gale, Kennesaw, GA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 432 days.

(21) Appl. No.: 12/878,937

(22) Filed: Sep. 9, 2010

(65) Prior Publication Data

US 2011/0009948 A1  Jan. 13, 2011

Related U.S. Application Data

(62) Division of application No. 11/205,254, filed on Aug. 15, 2005, now abandoned.

(51) Int. Cl.
*B29C 57/00* (2006.01)
*B29C 71/00* (2006.01)
*B29C 59/02* (2006.01)
*A61F 2/06* (2013.01)

(52) U.S. Cl.
USPC .......... 264/322; 264/234; 264/235; 264/320; 264/324; 623/1.15; 623/1.51; 623/1.54

(58) Field of Classification Search
None
See application file for complete search history.

(56) References Cited

U.S. PATENT DOCUMENTS

| | | | |
|---|---|---|---|
| 3,096,560 A * | 7/1963 | Liebig | 28/143 |
| 3,463,158 A * | 8/1969 | Schmitt et al. | 606/154 |
| 4,834,755 A * | 5/1989 | Silvestrini et al. | 623/13.19 |
| 4,942,875 A * | 7/1990 | Hlavacek et al. | 606/230 |
| 4,950,258 A * | 8/1990 | Kawai et al. | 604/530 |
| 4,997,440 A * | 3/1991 | Dumican | 623/1.38 |
| 5,178,630 A * | 1/1993 | Schmitt | 623/1.52 |
| 5,217,495 A * | 6/1993 | Kaplan et al. | 623/13.18 |
| 5,383,925 A * | 1/1995 | Schmitt | 623/1.53 |
| 5,591,222 A * | 1/1997 | Susawa et al. | 606/195 |
| 5,629,077 A * | 5/1997 | Turnlund et al. | 623/1.15 |
| 5,670,161 A | 9/1997 | Healy et al. | |
| 5,766,710 A * | 6/1998 | Turnlund et al. | 623/1.15 |
| 6,099,557 A * | 8/2000 | Schmitt | 623/1.1 |
| 6,130,271 A * | 10/2000 | Jarrett et al. | 523/113 |
| 6,147,135 A | 11/2000 | Yuan et al. | |
| 6,240,615 B1 * | 6/2001 | Kimes et al. | 29/516 |
| 6,441,267 B1 * | 8/2002 | Dugan | 604/370 |
| 6,491,720 B1 | 12/2002 | Vallana et al. | |
| 6,569,191 B1 * | 5/2003 | Hogan | 623/1.11 |
| 6,585,755 B2 | 7/2003 | Jackson et al. | |
| 6,589,468 B1 * | 7/2003 | Schmitt | 264/257 |
| 6,626,939 B1 * | 9/2003 | Burnside et al. | 623/1.38 |

(Continued)

FOREIGN PATENT DOCUMENTS

| | | |
|---|---|---|
| EP | 0 668 083 | 8/1995 |
| EP | 1 607 109 | 12/2005 |
| WO | WO 93/16661 | 9/1993 |
| WO | WO 03/034940 | 5/2003 |

OTHER PUBLICATIONS

Invitation to pay additional fees for PCT/US2006/030169 filed Aug. 1, 2006, mailed Dec. 20, 2007, 6 pgs.

(Continued)

*Primary Examiner* — Jeffrey Wollschlager
(74) *Attorney, Agent, or Firm* — Squire Sanders (US) LLP

(57) ABSTRACT

Polymeric composite stents reinforced with fibers for implantation into a bodily lumen are disclosed.

12 Claims, 7 Drawing Sheets

(56) References Cited

U.S. PATENT DOCUMENTS

| | | | |
|---|---|---|---|
| 6,769,161 B2 * | 8/2004 | Brown et al. | 29/234 |
| 6,773,459 B2 * | 8/2004 | Dauner et al. | 623/13.18 |
| 6,814,753 B2 * | 11/2004 | Schmitt | 623/1.44 |
| 2002/0019661 A1 * | 2/2002 | Datta et al. | 623/1.15 |
| 2002/0052612 A1 * | 5/2002 | Schmitt et al. | 606/151 |
| 2003/0083732 A1 | 5/2003 | Stinson | |
| 2003/0135265 A1 * | 7/2003 | Stinson | 623/1.16 |
| 2003/0216804 A1 | 11/2003 | DeBeer et al. | |
| 2004/0044397 A1 | 3/2004 | Stinson | |
| 2004/0146546 A1 * | 7/2004 | Gravett et al. | 424/445 |
| 2005/0021131 A1 * | 1/2005 | Venkatraman et al. | 623/1.19 |
| 2006/0018948 A1 | 1/2006 | Guire et al. | |
| 2006/0287710 A1 | 12/2006 | Lendlein et al. | |

OTHER PUBLICATIONS

Middleton et al., "Synthetic biodegradable polymers as orthopedic devices", Biomaterials, vol. 21, pp. 2335-2346 (2000).

Rodriguez, Principles of Polymer Systems $2^{nd}$ ed., McGraw Hill (1982), 4 title pages.

* cited by examiner

FIBER REINFORCED COMPOSITE STENTS

CROSS-REFERENCE TO RELATED APPLICATIONS

This application is a division of co-pending U.S. patent application Ser. No. 11/205,254, filed on 15 Aug. 2005, which is incorporated by reference as if fully set forth, including any figures, herein.

BACKGROUND OF THE INVENTION

1. Field of the Invention

This invention relates to radially expandable implantable medical devices such as stents for implantation into a bodily lumen. In particular, the invention relates composite stents reinforced with fibers.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. Conventional methods of constructing a stent from a polymer material involve extrusion, blow molding, or injection molding a polymer tube based on a single polymer or polymer blend and then laser cutting a pattern into the tube. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

In general, there are several important aspects in the mechanical behavior of polymers that affect stent design. Polymers tend to have lower strength than metals on a per unit mass basis. Therefore, polymeric stents typically have less circumferential strength and radial rigidity than metallic stents of the same or similar dimensions. Inadequate radial strength potentially contributes to a relatively high incidence of recoil of polymeric stents after implantation into vessels.

Another potential problem with polymeric stents is that their struts or bar arms can crack during crimping and expansion, especially for brittle polymers. The localized portions of the stent pattern subjected to substantial deformation tend to be the most vulnerable to failure. Furthermore, in order to have adequate mechanical strength, polymeric stents may require significantly thicker struts than a metallic stent, which results in an undesirably larger profile.

Additionally, another factor to consider in stent design is radiopacity. In addition to meeting the mechanical requirements described above, it is desirable for a stent to be radiopaque, or fluoroscopically visible under x-rays. "Radiopaque" refers to the ability of a substance to absorb x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

A significant shortcoming of polymers as compared to metals (and polymers generally composed of carbon, hydrogen, oxygen, and nitrogen) is that they are radiolucent with no radiopacity. Polymers tend to have x-ray absorption similar to body tissue.

Additionally, there are manufacturing difficulties in placing small markers on stents as well as challenges in keeping very small markers attached to the stent. If the maximum permissible size of the marker is too small to be visible on a fluoroscope, multiple markers may be necessary. This makes manufacturing even more challenging.

Therefore, it would be desirable to have methods of making biodegradable polymeric stents that are both strong and flexible.

SUMMARY OF THE INVENTION

Certain embodiments of the present invention are directed to a method of making a stent that may include forming a mixture having a matrix polymer and a plurality of short fibers such that fibers include a material having a melting temperature greater than a melting temperature of the matrix polymer. The method may further include disposing the mixture in a tube or sheet forming apparatus to form a tube or a sheet such that the apparatus is heated so that a temperature of the mixture in the apparatus is greater than the melting temperature of the matrix polymer and less than the melting temperature of the material of the fibers. At least a portion of the matrix polymer may be a polymer melt. A stent may be fabricated from the tube or sheet including the matrix polymer and the short fibers.

Further embodiments of the present invention are directed to a method of making a stent that may include forming a tube having at least one fiber layer and at least one polymer film layer such that fibers of at least one fiber layer include a material having a melting temperature greater than a melting temperature of at least one polymer film layer. The method may further include heating the tube to a temperature greater than the melting temperature of at least one polymer film layer and less than the melting temperature of the material of the fibers to melt at least a portion of the polymer of at least one polymer film layer. At least a portion of at least one fiber layer may become embedded within at least a portion of the melted polymer of at least one polymer film layer. The heated tube may then be cooled and a stent fabricated from the cooled tube.

Additional embodiments of the present invention are directed to a method of making a stent that may include forming a layered sheet having at least one fiber layer and at least one polymer film layer such that fibers of at least one fiber layer include a material having a melting temperature greater than a melting temperature of at least one polymer film layer. The method may further include heating the layered sheet to a temperature greater than the melting temperature of at least one polymer film layer and less than the melting temperature of the material of the fibers to melt at least a portion of the polymer of at least one polymer film layer. At least a portion of the fibers may become embedded within at least a portion of the melted polymer of at least one polymer film layer. The heated layered sheet may then be cooled and a stent fabricated from the cooled sheet.

Additional embodiments of the present invention are directed to a method of making a stent that may include forming a coating layer comprising a coating polymer over a tube-shaped fiber layer having a plurality of fibers. The coating layer may be formed by applying a fluid including the coating polymer dissolved in a solvent and by removing all or a majority of the solvent from the applied fluid. The fibers may include a material that is insoluble or having a relatively low solubility in the solvent. The material may have a melting temperature greater than a melting temperature of the coating polymer. The method may further include fabricating a stent from the coated fiber layer.

Other embodiments of the present invention are directed to a method of making a stent that may include disposing a plurality of fibers within a mold for forming a structure. The method may further include disposing a matrix polymer that is partially or completely molten into the mold to at least partially embed the fibers within the molten polymer. The fiber may include a material having a melting temperature greater than a melting temperature of the matrix polymer. A temperature of the matrix polymer and the fibers in the mold may be less than the melting temperature of the material. The method may further include cooling the molten polymer to form the structure and fabricating a stent from the cooled structure.

Further embodiments of the present invention are directed to a method of making a stent that may include disposing a plurality of fibers in an extruder for forming a structure. The method may further include conveying a matrix polymer into the extruder. The fibers may include a material having a melting temperature greater than a melting temperature of the matrix polymer. The structure may be formed with the extruder at a temperature greater than the melting temperature of the matrix polymer and less than the melting temperature of the material in such a way that at least some of the fibers become embedded within the matrix polymer. A stent may then be fabricated from the cooled structure.

Additional embodiments of the present invention are directed to a method of making a stent that may include heating a fiber mesh tube including two types of fibers. A first fiber may include a first polymer and the second fiber may include a second polymer. The first polymer may have a softening temperature lower than a softening temperature of the second polymer. The tube may be heated to a temperature range between the softening temperature of the first polymer and the softening temperature of the second polymer. The method may further include applying pressure to the tube so as to flatten at least some of the fibers of the tube to reduce a radial profile of the tube.

Some further embodiments of the present invention are directed to a method of making a stent that may include heating a fiber mesh tube. At least some of the fibers of the tube may include a first polymer and a second polymer. The first polymer may have a softening temperature lower than a softening temperature of the second polymer. The tube may be heated to a temperature range between the softening temperature of the first polymer and the softening temperature of the second polymer. The method may further include applying pressure to the tube so as to flatten at least some of the fibers of the tube to reduce a radial profile of the tube.

Some further embodiments of the present invention are directed to a method of making a stent that may include coupling a metallic film to at least a portion of a surface of a polymeric tube. The method may further include fabricating a stent from the tube with the metallic film so that the metallic film is over at least a portion of a surface of the stent.

Other embodiments of the present invention are directed to a method of making a stent that may include forming a tube having a metallic film in between two radial polymeric layers. The method may further include fabricating a stent from the tube.

Certain other embodiments of the present invention are directed to a method of making a stent that may include elongating a polymeric tube so that a diameter of the stent decreases. The method may further include positioning a metallic band around a circumference of the elongated tube. The elongated polymeric tube with the metallic band positioned around the tube may then be heated. The method may further include allowing the heated tube to radially expand so as to couple the metallic band to the tube. A stent may be fabricated from the expanded tube.

Additional embodiments of the present invention are directed to a radially expandable stent including a plurality of interconnecting structural elements including fibers at least partially embedded in a matrix polymer. The fibers may include a material having a melting temperature greater than a melting temperature of the matrix polymer. The fibers may be configured to provide mechanical reinforcement to the stent due to a higher strength and modulus along an axis of the fibers than the matrix polymer.

Other embodiments of the present invention are directed to a radially expandable stent including a plurality of interconnecting structural elements including at least one radial fiber layer and at least one radial polymer film layer. The fibers may include material with a melting temperature greater than a melting temperature than at least one polymer film layer. At least one fiber layer may be at least partially embedded within at least one polymer film layer. The fibers may be configured to provide mechanical reinforcement to the stent due to a higher strength and modulus along an axis of the fibers than the polymer film layer.

Additional embodiments of the present invention are directed to a radially expandable stent including a plurality of structural elements including at least two radial fiber layers and at least one radial polymer film layer. At least a portion of at least one fiber layer may be embedded within at least a portion of at least one polymer film layer. An orientation of fibers relative to a cylindrical axis of the stent of at least one fiber layer may be different from an orientation of fibers in another fiber layer.

Certain embodiments of the present invention are directed to a radially expandable stent woven from at lease two types of fibers. A first fiber may include a first polymer and the second fiber may include a second polymer. The first polymer may have a softening temperature lower than a softening temperature of the second polymer. At least some of the fibers may have a flattened radial profile that reduces the radial profile of the tube.

Other embodiments of the present invention are directed to a radially expandable stent woven from fibers comprising a first polymer and a second polymer. The first polymer may have a softening temperature lower than a softening temperature of the second polymer such that at least some of the fibers have a flattened radial profile that reduces the radial profile of the tube.

Additional embodiments of the present invention are directed to a radially expandable stent including a metallic film coupled to a plurality of portions of a surface of the stent such that the metallic film is sufficiently radiopaque to allow the stent to be visualized during use Further embodiments of the present invention are directed to a radially expandable stent including a plurality of interconnecting structural elements such that the structural elements may have two radial polymeric layers with metallic film embedded in a plurality of locations in between the layers. The metallic film may be sufficiently radiopaque to allow the stent to be visualized during use.

DETAILED DESCRIPTION OF THE INVENTION

Figure 1:
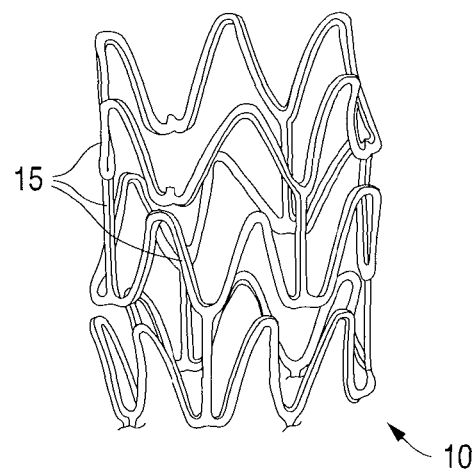
FIG. 1 depicts a three-dimensional view of a stent.

Various embodiments of the present invention relate to composite polymeric biodegradable implantable medical devices and methods of making such devices. In general, a composite implantable medical device is a device which is made up of two or more macroscopically distinct materials that have different properties. The composite device as a whole may have desirable properties of two or more of the distinct materials. Therefore, desirable mechanical and/or degradation properties may be obtained through the use of a polymer composite structure.

For the purposes of the present invention, the following terms and definitions apply:

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. The "strength" of a solvent refers to the degree to which a solvent may dissolve a polymer. The stronger a solvent is, the more polymer the solvent can dissolve.

Furthermore, a property of a material that quantifies a degree of strain with applied stress is the modulus. "Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its $T_g$, a polymer tends to be brittle with a high modulus. As the temperature of a polymer is increased from below to above its $T_g$, its modulus decreases.

"Above" a surface or layer is defined as higher than or over a surface or layer measured along an axis normal to a surface or layer, but not necessarily in contact with the surface or layer.

"Vicat Softening Temperature" (VST) is a measure of the temperature at which a polymer starts to soften at specified test conditions according to ISO 306. It is determined with a standard indenter (a flat-ended needle of 1 mm 2 circular cross section) penetrating into the surface of a test specimen under a predefined load. The temperature at 1 mm penetration is quoted as the VST in Co. VST gives an indication of a material's ability to withstand limited short-term contact with a heated object.

The term "elastic deformation" refers to deformation of an object in which the applied stress is small enough so that the object moves towards its original dimensions or essentially its original dimensions once the stress is released. However, an elastically deformed polymer material may be prevented from returning to an undeformed state if the material is below the $T_g$ of the polymer. Below $T_g$, energy barriers may inhibit or prevent molecular movement that allows deformation or bulk relaxation.

"Elastic limit" refers to the maximum stress that a material will withstand without permanent deformation. The "yield point" is the stress at the elastic limit and the "ultimate strain" is the strain at the elastic limit. The term "plastic deformation" refers to permanent deformation that occurs in a material under stress after elastic limits have been exceeded.

The term "implantable medical device" is intended to include, but not limited to, self-expandable stents, balloon-expandable stents, stent-grafts, and grafts. In general, an implantable medical device, such as a stent, can have virtually any structural pattern that is compatible with a bodily lumen in which it is implanted. The embodiments of the invention described herein are generally applicable to implantable medical devices.

Typically, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency. A myriad of strut patterns are known in the art for achieving particular design goals.

FIG. 1 depicts a three-dimensional view of a stent 10 which shows struts 15. The embodiments disclosed herein are not limited to stents or to the stent pattern illustrated in FIG. 1. The embodiments are easily applicable to other patterns and other devices. The variations in the structure of patterns are virtually unlimited.

A stent such as stent 10 may be fabricated from a tube by forming a pattern with a technique such as laser cutting. Representative examples of lasers that may be used include an excimer, carbon dioxide, and YAG. In other embodiments, chemical etching may be used to form a pattern on the elongated tube.

In some embodiments, the diameter of the polymer tube prior to fabrication of an implantable medical device may be between about 0.2 mm and about 5.0 mm, or more narrowly between about 1 mm and about 3 mm. Unless otherwise specified, the "diameter" of the tube refers to the outside diameter of the tube.

Various embodiments of fabricating composite polymeric implantable devices are disclosed herein. The continuous and discrete phases may include polymeric or metallic materials or a combination of polymeric and metallic materials.

In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed, and/or eliminated by the body. In addition, a medicated stent may be fabricated by coating the surface of the stent with an active agent or drug, or a polymeric carrier including an active agent or drug.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration can be from about a month to a few years, but is typically in the range of six to eighteen months.

Biodegradation of polymers generally refers to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel. The decrease in molecular weight may be caused by, for example, hydrolysis and/or metabolic processes. Hydrolysis is a chemical process in which a molecule is cleaved into two parts by the addition of a molecule of water.

Consequently, the degree of bulk degradation of a polymer is strongly dependent on the diffusivity, and hence the diffusion rate of water in the polymer. Several characteristics or parameters of the degradation process are important in designing biodegradable devices. These include an average erosion rate of a device, the erosion profile, the half-life of the degrading polymer, and mechanical stability of a device during the degradation process. The "average erosion rate" may be an average erosion rate over any selected time interval:

$$\text{Average erosion rate} = (m_2 - m_1)/(t_2 - t_1)$$

where "m" refers to mass of the device, "t" refers to a time during erosion, and $m_1$ and $m_2$ are the masses of the device at $t_1$ and $t_2$ during erosion. For instance, the selected time interval may be between the onset of degradation and another selected time. Other selected times, for example, may be the time for about 25%, 50%, 75%, or 100% (complete erosion) of the device to erode. Complete erosion may correspond approximately to the time required for treatment by the device.

The "half-life" of a degrading polymer refers to the length of time for the molecular weight of the polymer to fall to one half of its original value. See e.g., J. C. Middleton and A. J. Tipton, Biomaterials, Vol. 21 (23) (2000) pp. 2335-2346.

In addition, metals may be considered to be biostable or bioerodible. Some metals are considered bioerodible since they tend to erode or corrode relatively rapidly when exposed to bodily fluids. Biostable metals refer to metals that are not bioerodible. Biostable metals have negligible erosion or corrosion rates when exposed to bodily fluids.

In general, metal erosion or corrosion involves a chemical reaction between a metal surface and its environment. Erosion or corrosion in a wet environment, such as a vascular environment, results in removal of metal atoms from the metal surface. The metal atoms at the surface lose electrons and become actively charged ions that leave the metal to form salts in solution.

Representative examples of bioerodible metals that may be used to fabricate an implantable medical device may include, but are not limited to, magnesium, zinc, and iron. In one embodiment, a bioerodible metallic stent may be completely eroded when exposed to bodily fluids, such as blood, between about a week and about three months, or more narrowly, between about one month and about two months.

As indicated above, implantable medical devices, such as a stent, should be capable of exhibiting relatively high strength and rigidity, as well as flexibility since devices have varied mechanical requirements during use arising from stress imposed on the device, both before and during treatment. "Use" includes manufacturing, assembling (e.g., crimping a stent on balloon), delivery of a stent through a bodily lumen to a treatment site, and deployment of a stent at a treatment site. For example, a stent requires radial or hoop strength and rigidity to resist radial compressive forces.

The stress imposed on a stent, for example, during use subjects individual structural elements to stress. During deployment, the scaffolding and/or coating of a stent can be exposed to stress caused by the radial expansion of the stent body. In addition, the scaffolding and/or coating may be exposed to stress when it is mounted on a catheter from crimping or compression of the stent. After deployment, radial compressive forces subject scaffolding and/or coating to stress. These stresses can cause the scaffolding to fracture. Failure of the mechanical integrity of the stent while the stent is localized in a patient can lead to serious risks for a patient. For example, there is a risk of embolization caused by a piece of the polymeric scaffolding and/or coating breaking off from the stent.

Conventional methods of constructing a stent from a polymer material involve forming a polymer tube based on a single polymer or polymer blend and then laser cutting a pattern into the tube. Alternatively, a polymer tube may be formed from sheets or films that are rolled and bonded. Polymer tubes and sheets may be formed by various methods, including, but not limited to extrusion, injection molding, or blow molding.

In extrusion, a polymer melt of a single polymer or polymer blend is conveyed through an extruder which is then formed into a tube. Extrusion tends to impart large forces on the molecules in the axial direction of the tube due to shear forces on the polymer melt. The shear forces arise from forcing the polymer melt through a die and pulling and forming the polymer melt into the small dimensions of a tube. As a result, polymer tubes formed by conventional extrusion methods tend to possess a significant degree of axial polymer chain alignment. However, such conventionally extruded tubes tend to possess no or substantially no polymer chain alignment in the circumferential direction.

Due to stresses imposed on an implantable medical device during use, it is important for the mechanical stability of a device to have an adequate magnitude of strength both in axial and circumferential directions. The direction of stress in structural members can be in various directions between axial and circumferential. Therefore, an adequate balance of axial and circumferential strength is also important for mechanical stability. The relative amount of axial and circumferential orientation may depend on a number of factors such as the stent pattern.

A radially expandable device, such as a stent, without an adequate magnitude and balance of strength in axial and circumferential directions may tend to be more prone to mechanical instability. For example, a stent made from a tube with an adequate magnitude and balance of strength in the radial and axial directions may be less susceptible to cracking during crimping and deployment. Therefore, it may be desirable to fabricate an implantable medical device with desired strength and balance in the axial and circumferential directions.

Desired strength in both directions may be achieved in a number of ways. Some embodiments may include fabricating a device from a tube of a composite structure with fibers mixed with a continuous phase. In other embodiments, polymer chain alignment may be induced along the circumferential direction to increase strength.

In certain embodiments, a polymer for a fiber may be selected that can form crystalline regions with a high modulus and the polymer for a continuous phase may include a relatively flexible polymer. Representative examples of polymers that may be used for fiber reinforcement include, but are not limited to, poly(L-lactide) and polyglycolide. Representative polymers that may be used for a continuous phase may include, but are not limited to, poly(DL-lactide) and poly(ε-caprolactone).

An implantable medical device, such as a stent, with an adequate magnitude and balance of both circumferential strength and modulus may be less susceptible to cracking during the crimping process. In addition, increased circumferential strength and modulus may allow a decrease in strut width, or generally, a decrease in form factor of a stent. Implantable medical devices fabricated from tubes with adequate strength in both the axial and circumferential directions may possess mechanical properties similar to or better than metal stents with an acceptable wall thickness and strut width.

It is well know by those skilled in the art that molecular orientation or alignment of polymer chains in a polymer is a particularly important phenomenon that strongly influences bulk polymer properties. For example, strength, modulus, yield stress behavior, and elongation to break are a few of the important properties that may be influenced by orientation of polymer chains in a polymer. Orientation refers to the degree of alignment of polymer chains along a longitudinal or covalent axis of the polymer chains. The degree of molecular orientation in a polymeric material may be induced by applying stress along a preferred direction.

Polymers in the solid state may have amorphous regions and crystalline regions. Crystalline regions include highly oriented polymer chains in an ordered structure. An oriented crystalline structure tends to have high strength and high modulus (low elongation with applied stress) along an axis of alignment of polymer chains. On the other hand, amorphous polymer regions include relatively disordered polymer chains that may or may not be oriented in a particular direction. However, a high degree of molecular orientation may be induced even in an amorphous region. An oriented amorphous region also tends to have high strength and high modulus along an axis of alignment of polymer chains. Additionally, for some polymers under some conditions, induced orientation in an amorphous polymer may be accompanied by crystallization of the amorphous polymer.

A polymer may be completely amorphous, partially crystalline, or almost completely crystalline. A partially crystalline polymer includes crystalline regions separated by amorphous regions. The polymer chains of the crystalline regions are not all necessarily oriented in the same direction. However, a high degree of orientation of crystallites may be induced by applying stress to a semi-crystalline polymer. The stress may also induce orientation of polymer chains in amorphous regions of a polymer.

Polymer tubes fabricated in a conventional manner using extrusion, blow molding, or injection molding based on a single polymer or polymer blend tend to have inadequate strength and rigidity in the circumferential direction. This is due to low polymer chain alignment in the circumferential direction.

Various embodiments of the present invention include implantable medical devices, such as stents, and methods of fabricating such devices from a composite including a continuous phase and a discrete phase. The continuous phase may include a polymeric matrix and the discrete phase may include fibers mixed, dispersed, and/or embedded in the matrix. Additionally, either or both the continuous phase or the discrete phase may include an active agent.

In some embodiments, the discrete phase may include radiopaque materials. The radiopaque materials may include, for example, metals; alloys; or mixtures of polymers and metal or alloys. In one embodiment, the discrete phase may include metallic fibers, wires, bands, or strips. The metals may include erodible metals, biostable metals, or mixtures of biostable and bioerodible metals. Representative metals that may be used in the discrete phase may include, but are not limited to, magnesium, zinc, iron, platinum, and gold.

A "fiber" may be defined as a unit of matter having a length substantially longer than its width or diameter. As used herein, a fiber can include, but is not limited to, a filament, a strip, or a wire.

In some embodiments, a polymeric fiber may be formed using any of a number of methods known in the art including, but not limited to, melt spinning, wet spinning, dry spinning, gel spinning, electrospinning, or an atomizing process. Fibers may be fabricated with relatively high polymer chain orientation along the fiber axis, and thus relatively high strength and stiffness.

"Spinning" of polymeric fibers generally involves the extrusion or forcing of a thick, viscous fluid, which is either a polymer melt or solution, through the tiny holes of a device called a spinneret to form continuous filaments of semi-solid polymer. The spinneret has a multiplicity of holds through which polymer melt or solution pass through. In their initial state, the fiber-forming polymers are solids and therefore must be first converted into a fluid state for extrusion. This is usually achieved by melting, if the polymers are thermoplastic (i.e., they soften and melt when heated), or by dissolving them in a suitable solvent if they are non-thermoplastic. If they cannot be dissolved or melted directly, they must be chemically treated to form soluble or thermoplastic derivatives.

In melt spinning, the fiber-forming polymer is melted for extrusion through the spinneret and then solidified by cooling. Wet spinning involves forming a fiber from a polymer dissolved in a solvent. The polymer solution is pumped through a spinneret that is submerged in a chemical bath. The dissolved polymer is immiscible in the chemical bath. As the filaments emerge from the spinneret, the polymer precipitates from solution and solidifies.

Dry spinning also involves forming fibers from a polymer solution. The polymer solution is pumped through the spinneret. However, instead of precipitating the polymer by dilution or chemical reaction, solidification is achieved by evaporating the solvent in a stream of air or inert gas.

Gel Spinning is a type of wet spinning, but is a special process used to obtain high strength or other special fiber properties. In this process, ultra-high molecular weight polymer is dissolved in a solvent at very low concentration. The concentration is much lower than that typically used in wet spinning and dry spinning processes. The polymers or fibers precipitate from solution and solidify in a chemical bath or in a chilled water bath. The fiber is then drawn to orient the polymer molecules. The draw-down ratio is also typically much higher than for wet spinning and dry spinning processes.

The draw-down ratio is defined as the ratio of the length of a drawn fiber to the original length of the fiber. The draw-down ratio for gel spinning can be up to 40:1, while the drawn-down ratio for wet or melt spinning can be about 3-15:1.

The draw-down ratio is defined as the ratio of the length of a drawn fiber to the length of an as-spun fiber. The as-spun fiber refers to a solidified fiber formed from solution or melt. The draw-down ratio for gel spinning can be up to 40:1, while the drawn-down ratio for wet or melt spinning can be about 3-15:1.

In a dry-jet-wet spinning method, the polymer is not in a true liquid state during extrusion. The polymer chains are bound together at various points in liquid crystal form. The chains are not completely separated, as they would be in a true solution. This produces strong inter-chain forces in the resulting filaments that can significantly increase the tensile strength of the fibers. In addition, the liquid crystals are aligned along the fiber axis by the shear forces during extrusion. The filaments emerge with a relatively high degree of orientation relative to each other, further enhancing strength. The filaments first pass through air and then are cooled further in a liquid bath. The draw-down ratio in dry-jet-wet spinning is typically less than 1.03:1.

Electrospinning and atomizing processes may be used to produce nanofibers. A "nanofiber" refers to a fiber with a dimension in the range of about 1 nm to about 10,000 nm. Electrospinning makes use of electrostatic and mechanical force to spin fibers from the tip of a fine orifice or spinneret. In electrospinning, a polymer is dissolved in a solvent or a polymer melt and is placed in a spinneret (e.g., a glass pipette) sealed at one end. The spinneret is maintained at positive or negative charge by a power supply, for example. When the electrostatic repelling force overcomes the surface tension force of the polymer solution or melt, the liquid spills out of the spinneret and forms an extremely fine continuous filament.

The strength and modulus of the spun fibers may be increased by drawing. Drawing involves applying tension along the fiber axis. Fibers may be drawn while extruded fibers are solidifying and/or after they have hardened. Drawing tends to pull the molecular chains together and orient them along the fiber axis, creating a considerably stronger and rigid fiber along the fiber axis.

As indicated above, favorable mechanical and degradation properties of a stent may be obtained by fabricating the stent as a composite. Individual characteristics of the stent (i.e., rigidity, strength, longitudinal flexibility, degradation rate) may be provided by one or more of the macroscopically distinct materials that make up the composite. Thus, one benefit of a composite structure is that individual characteristics of a stent may be tuned independently or more independently than a stent fabricated from a single polymer or blend.

To provide strength and rigidity to a stent, the fiber may be fabricated to be relatively strong and stiff with a high modulus along the fiber axis. The continuous phase may be configured to have different properties than the discrete fiber phase. For instance, the continuous phase may be configured to have a lower modulus, and thus greater flexibility than the discrete phase. Therefore, the continuous phase may be configured to provide the required flexibility for the stent. As indicated above, polymers below their $T_g$ tend to be relatively brittle or inelastic and are more flexible and more easily deformed than above their $T_g$. Therefore, a flexible continuous phase may be obtained by using polymers with a $T_g$ above a body temperature.

Additionally, the degradation behavior of the fiber and continuous phases may be configured to have various combinations. In one embodiment, degradation rates of the fiber and continuous phase may be approximately the same. Alternatively, the degradation rates of the fiber and the continuous phases may be different. The degradation rate of the fiber may be faster or slower than the continuous phase. As discussed herein, the degradation rate of phases may be controlled the choice of polymer, the molecular weight, and the crystallinity of the polymers of the phases.

Moreover, there are numerous ways that the properties of polymers in the stent may be controlled or modified. These include a suitable choice of polymers or chemical component groups in polymers for the discrete and continuous phases since different polymers have different mechanical properties and degradation rates. In addition, as described below, various properties depend on the molecular weight of polymers. In addition, certain properties of polymers are also related to the degree of crystallinity in a polymer. Thus, these properties of the discrete and continuous phases may be modified independently by choice of polymers and modifying the molecular weight and crystallinity of the polymers in these phases.

Mechanical properties such as strength and modulus, the degradation behavior of polymer, and melting temperatures depend upon the molecular weight. In general, the higher the molecular weight, the stronger and stiffer (higher modulus) a polymer is. Therefore, the strength and modulus of a fiber may be further enhanced by fabricating a fiber with a higher molecular weight.

Additionally, the degradation rate of a polymer decreases as the molecular weight increases. Also, the melting temperature increases with molecular weight. In some embodiments, the same type of polymer with different molecular weights may be used for both the fiber and continuous phase in a composite for a device. Due to the different molecular weight of the continuous and discrete phases, the mechanical properties, degradation behavior, and melting temperature of the phases may be different.

As indicated above, the degree of crystallinity in a polymer is related to the mechanical properties such as the strength and modulus of a material. The higher the degree of crystallinity, the stronger and stiffer a polymer is along the direction of molecular orientation of crystalline structures in the polymer.

In addition, the degree of crystallinity is also related to the diffusion rate of fluids, and hence, the erosion rate of a biodegradable polymer. In general, the diffusion rate of a fluid through a polymer decreases as the degree of crystallinity increases. Therefore, it is expected that the diffusion rate of water and bodily fluids is lower in crystalline and semi-crystalline polymers than in amorphous polymers. Thus, the erosion rate of a biodegradable polymeric region may be controlled by modifying the degree of crystallinity in a continuous polymeric phase of a composite, for example.

In one embodiment, the crystallinity of a polymer may be modified by heating the polymer. Heating a polymer can alter the degree of crystallinity and/or size of crystalline regions in a polymer material. The degree of crystallinity may be altered by heating the polymer within a particular temperature range. Heating a polymer material to a temperature below the glass transition temperature, $T_g$, of the polymer does not significantly alter the molecular structure, and hence, the mechanical properties of the material. Below $T_g$, energy barriers to segmental motion of the chains of a polymer inhibit or prevent alteration of molecular structure of a polymeric material.

In general, crystallization may occur in a polymeric material that is heated to a temperature between $T_g$ and the melting temperature, $T_m$, of the polymer. As a result, heating a polymer to a temperature between the $T_g$ and the $T_m$ of the polymer increases the modulus of the polymer.

Figure 2:
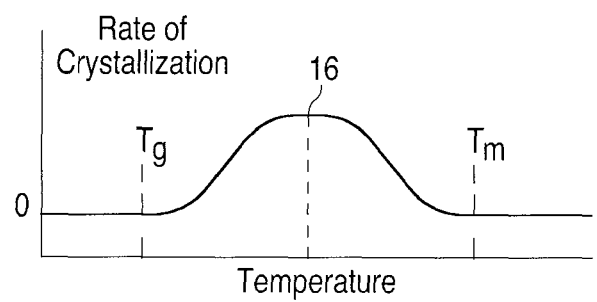
FIG. 2 depicts a schematic plot of the rate of crystallization of a polymer as a function of temperature.

FIG. 2 depicts a schematic plot of the rate of crystallization of a polymer as a function of temperature. (Rodriguez, F., *Principles of Polymer Systems*, $2^{nd}$ ed., McGraw Hill (1982)) FIG. 2 shows that the rate of polymer crystallization increases as the temperature is increased from below the $T_g$ of the polymer or is decreased from above the $T_m$ of the polymer. The rate of crystallization reaches a maximum 16 somewhere between the $T_g$ and the $T_m$. FIG. 2 shows that effectively no crystallization occurs below the $T_g$ or above the $T_m$.

In addition, as indicated above, an amorphous polymer may be formed by heating a polymer material. Above the $T_m$, a polymeric material becomes a disordered melt and cannot crystallize and any crystallinity present is destroyed. Quenching a polymer melt from above the $T_m$ of the polymer to a temperature below the $T_g$ of the polymer may result in the formation of a solid amorphous polymer. The resulting amorphous polymer material may have a lower modulus and be a more flexible or a less stiff material than before heating.

In certain embodiments, a method of fabricating a fiber-reinforced stent may include forming a mixture including a matrix polymer and a plurality of short or staple fibers. The fibers may include a material having a melting temperature greater than a melting temperature of the matrix polymer.

In one embodiment, the matrix polymer may be a biostable or biodegradable polymer or a combination thereof. The material of the fibers may also be a biostable or biodegradable polymer or a combination thereof. In some embodiments, the material of the fibers may be a biostable and/or erodible metal. In an embodiment, the fibers may be combination of a polymeric and a metallic material. For example, the fibers may be a mixture of polymeric and metallic particles.

Figure 3:
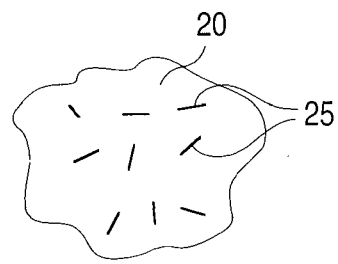
FIG. 3 depicts a schematic representation of a mixture of a continuous polymer phase and a discrete fiber phase.

As described above, the mixture formed may be a composite material. FIG. 3 depicts a schematic representation of the mixture. The matrix polymer may correspond to a continuous phase 20 and short fibers 25 may correspond to a discrete phase.

In one embodiment, the short fibers may be composed of the same or similar polymeric material as the continuous polymeric phase. Alternatively, the short fibers may be a mixture of fibers with different properties. For example, the short fibers may be a mixture of fibers having different degradation rates and/or mechanical properties.

In one embodiment, the mixture may be formed by mixing the matrix polymer and the fibers in a mixing apparatus at a temperature that is greater than the melting temperature of the matrix polymer and less than the melting temperature of the fiber material. Therefore, a polymeric melt continuous phase containing the matrix polymer may be mixed with a discrete fiber phase which is below the fiber material melting temperature.

Figure 4:
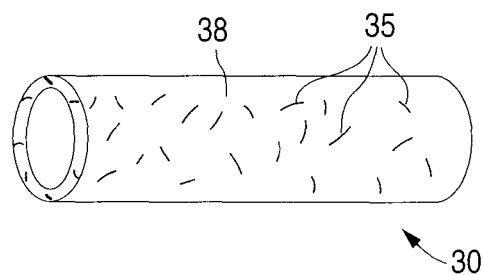
FIG. 4 depicts a fiber-reinforced tube with short fibers.

FIG. 4 depicts a fiber-reinforced tube with short fibers. Tube 30 includes a plurality of short fibers 35 embedded in a continuous polymer phase 38. As shown in FIG. 4, fibers 35 are oriented in arbitrary directions with respect to the axis of the tube. The fibers provide mechanical reinforcement axially, circumferentially, and orientations between the two. Thus, fibers enhance the mechanical stability of the tube and a stent formed from the tube.

In addition, circumferential strength can be further enhanced through radial expansion of the tube. Radial expansion enhances the circumferential strength of the tube due to induced polymer chain alignment of the continuous phase and induced circumferential alignment of the short fibers.

Embodiments of the method may further include disposing the mixture in a tube or sheet forming apparatus to form a tube or a sheet. The apparatus may be heated so that a temperature of the mixture in the apparatus is greater than the melting temperature of the matrix polymer and less than the melting temperature of the fiber material. In some embodiments, at least a portion of the matrix polymer may be a polymer melt. In addition, the mixture may then be cooled below the melting temperature of the matrix polymer.

As indicated above, a polymer melt may be cooled in such a way so as to control the degree of crystallinity of the formed tube. Thus, in some embodiments, the formed tube or sheet may be cooled to a temperature below the melting temperature of the matrix polymer such that a majority of the matrix polymer in the formed tube is either amorphous or crystalline.

In one embodiment, the forming apparatus may be an injection molding apparatus. The mixture may be injected at a temperature above the melting temperature of the matrix polymer and less than the melting temperature of the fiber such that at least a portion of the matrix polymer is a polymer melt. The mold may be heated by a heating device or in a chamber so that the temperature of the mixture in the mold is above the melting temperature of the matrix polymer and less than the melting temperature of the fibers.

Alternatively, in another embodiment, the mixture may be placed into the mold at a temperature below the melting temperature of the matrix polymer. The heated mold may then melt the matrix polymer by heating the mixture to a temperature above the melting temperature of the matrix polymer and less the melting temperature of the fibers.

In another embodiment, the forming apparatus may be an extruder. The mixture may be conveyed into the extruder at a temperature below the melting temperature of the matrix polymer. Alternatively, the mixture may be conveyed into the extruder at a temperature above the melting temperature of the matrix polymer and less than the melting temperature of the fiber such that at least a portion of the matrix polymer is a polymer melt. The mixture may be heated in the extruder so that its temperature is above the melting temperature of the matrix polymer and less than the melting temperature of the fiber.

Additionally, the method may further include fabricating a stent from the tube or sheet. As indicated above, a stent may be fabricated from a tube by forming a pattern on the tube including a plurality of interconnecting structural elements. Also, a sheet may be rolled into a tube and a pattern may be formed onto the tube.

Figure 5:
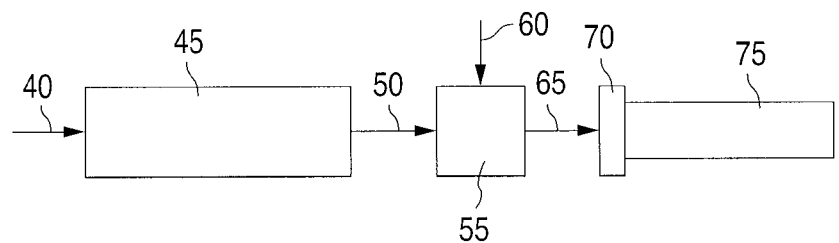
FIG. 5 depicts an embodiment of a method of fabricating a fiber reinforced tube.

FIG. 5 depicts a schematic representation of an embodiment of a method of fabricating a fiber reinforced tube, as described above. A matrix polymer 40 is conveyed into an extruder 45 as either a polymer melt or a solid. Extruder 45 melts and mixes polymer 40 to form a relatively low viscosity fluid 50. Fluid 50 is fed from extruder 45 into a mixing apparatus 55. Fibers 60 are also fed into mixing apparatus 55. Mixing apparatus 55 mixes fluid 50 with fibers 60 to produce mixture 65. Mixture 65 is conveyed through a die 70 into a forming apparatus 75 to form a tube or a sheet. Forming apparatus 75 may be, for example, an injection molding apparatus or an extruder.

In some embodiments, the short fibers may be made by forming fibers as described above, and cutting them into short lengths. In one embodiment, a length of at least a portion of the short fibers is substantially smaller than a diameter of the formed tube. For example, in some embodiments, the short fibers may be less than 0.05 mm long. In other embodiments, the short fibers may be between 0.05 and 8 mm long or more narrowly between 0.1 and 0.4 mm long or 0.3 and 0.4 mm long.

In other embodiments, a method of fabricating a fiber-reinforced stent may include forming a tube including at least one fiber layer and at least one polymer film layer. In one embodiment, at least one fiber layer alternates with at least one film layer. In an embodiment, fibers in a fiber layer may include at least one material having a melting temperature greater than melting temperatures at least one polymer film layer. Alternatively, the method may include forming a layered sheet including at least one fiber layer and at least one polymer film layer.

In one embodiment, at least one polymer film layer may include a biodegradable polymer. The material of the fibers of at least one fiber layer may include a biostable or biodegradable polymer or a combination thereof. In an embodiment, the material of the fibers of at least one fiber layer may include a biostable and/or erodible metal. In an embodiment, the fibers of at least one fiber layer may be a combination of a polymeric and a metallic material. For example, the fibers may be a mixture of polymeric and metallic particles.

In one embodiment, the fibers of the fiber layers may be composed of the same or similar polymeric material as the polymer film layers. Alternatively, the fiber layers may be a mixture of fibers with different properties. Some embodiments may include at least one fiber layer with different properties than another fiber layer. For example, different fiber layers may have different degradation rates and/or mechanical properties.

In other embodiments, the polymer film layers may have the same or similar properties. Alternatively, at least one polymer film layer may have different properties than another polymer film layer. For example, different polymer film layers may have different degradation rates and/or mechanical properties.

In one embodiment, the fiber layer may be a woven structure. A woven structure may refer to any structure produced from between one and several hundred or more fibers that are woven, braided, knitted, helically wound, and/or intertwined in any manner, at angles between 0° and 180° degrees with the cylindrical axis of the tube, depending upon the overall geometry and dimensions desired.

Figure 6A:
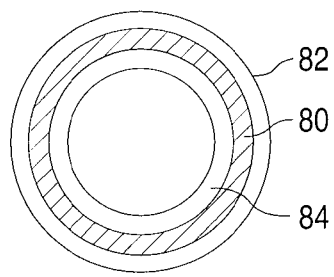
FIG. 6A depicts a two-dimensional radial cut-off view of a tube formed with a fiber layer and two polymer layers.
Figure 6B:
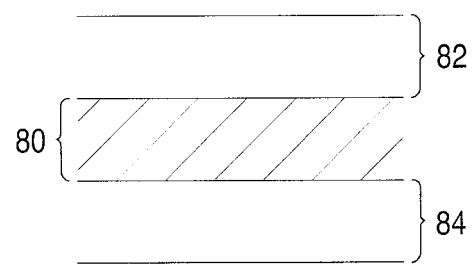
FIG. 6B depicts an expanded view of the layers from FIG. 6A.

FIG. 6A depicts a two-dimensional radial cut-off view of a tube formed with a fiber layer 80 between two polymer film layers 82 and 84. FIG. 6B depicts an expanded view of the layers. Fiber layer 80 is at least partially embedded in polymer from polymer film layers 82 and 84 due to melting of the polymer film layers.

Figure 7:
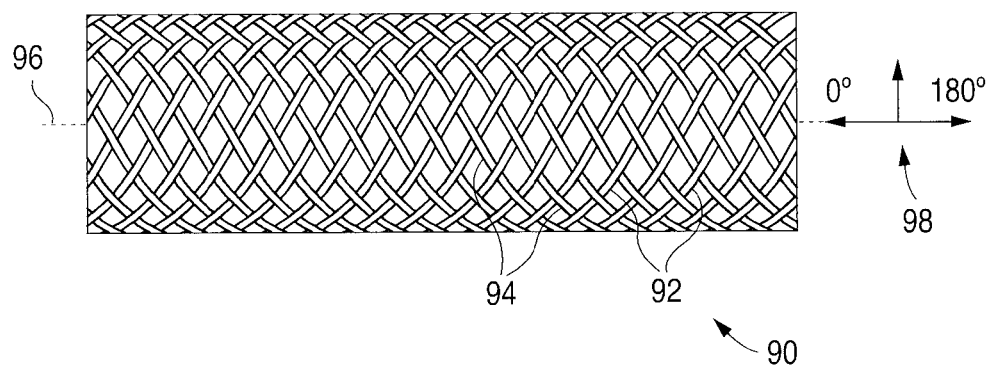
FIG. 7 depicts a tube of helically wound fiber mesh.

FIG. 7 depicts a tube 90 of helically wound fiber mesh including two sets of helically wound fibers 92 and 94. Tube 90 has a cylindrical axis 96. Coordinate system 98 shows the relative orientation with respect to axis 96. Fibers 92 have a relative orientation greater than 90° and fibers 92 have a relative orientation less than 90°.

In some embodiments, an orientation of fibers in one fiber layer may be different from an orientation of fibers in another fiber layer. This may further enhance the mechanical stability of stent. One embodiment may include one fiber layer with a set of fibers with an orientation greater than 90° and another fiber layer with a set of fibers with an orientation less than 90°.

Figure 8:
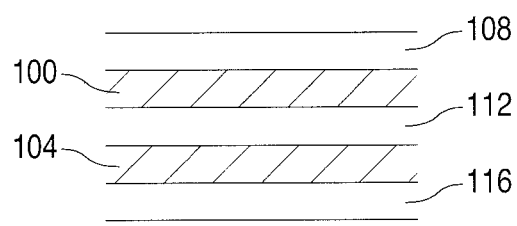
FIG. 8 depicts a two-dimensional view of layers of a tube formed with fiber layers and polymer layers.

For example, FIG. 8 depicts a two-dimensional view of layers of a tube formed with fiber layers 100 and 104 and polymer film layers 108, 112, and 116. Fiber layer 100 may include fibers with an orientation greater than 90°, such as fibers 92 in FIG. 7. Fiber layer 104 may include fibers with an orientation less than 90°, such as fibers 94 in FIG. 7.

Figure 9:
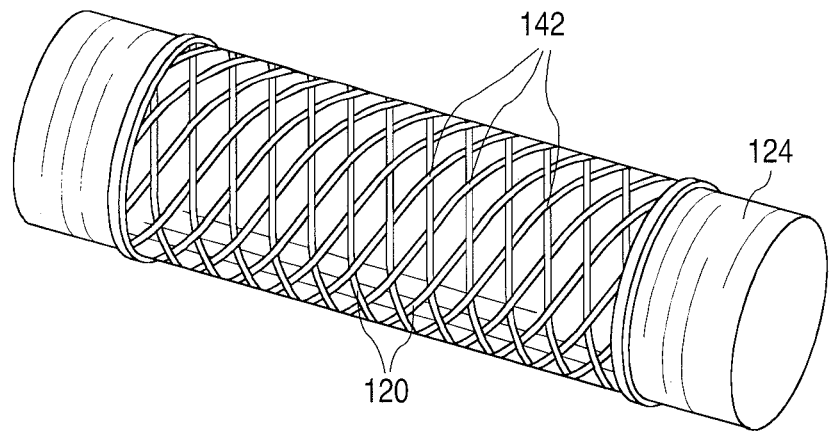
FIG. 9 depicts a fiber mesh tube disposed on a mandrel.

In one embodiment, the tube may be formed by disposing the layers over a mandrel. For example, FIG. 9 depicts a helically wound fiber mesh 120 disposed on a mandrel 124. A polymer film layer may be disposed over mandrel 124 before disposing fiber mesh 120 over mandrel 124. A polymer film layer may be disposed over mandrel 124 followed by another fiber layer, another polymer film layer, and so on.

Additionally, the method may further include heating the tube or sheet to a temperature greater than the melting temperatures of at least one polymer film layer and less than the melting temperature of a material of the fibers. Heating the tube or sheet may melt at least a portion of the polymer of the polymer film layers.

In one embodiment, at least a portion of the fiber layers may become embedded within at least a portion of the melted polymer of a polymer film layer. In some embodiments, the heated tube may be cooled and a stent may then be fabricated from the cooled tube. As described above, the heated tube may be cooled in such a way to control the degree crystallinity of the cooled polymer film layers of the formed tube.

As indicated above, nanofibers may be used in fabricating the stent. Nanofibers are particularly desirable when fabricating a layered structure since a larger number of layers may be formed. In general, the more the number of layers, the stronger the composite structure. The number of layers may be limited if fibers larger than nanofibers are used since the structure may become thicker than desirable.

In other embodiments, a method of fabricating a fiber-reinforced stent may include forming a coating layer including a coating polymer over a tube-shaped fiber layer having a plurality of fibers. Alternatively, the fibers may be formed into a sheet. The plurality of fibers shaped into a tube may be a woven structure, as described above.

In one embodiment, the coating polymer may include a biostable and/or biodegradable polymer or a combination thereof. A material of the fibers of at least one fiber layer may include a biostable and/or biodegradable polymer or a combination thereof. In an embodiment, the material of the fibers may include a biostable and/or erodible metal. In another embodiment, the fibers may be a combination of a polymeric and a metallic material. For example, the fibers may be a mixture of polymer and metallic particles.

In one embodiment, the coating layer may be formed by applying a fluid including the coating polymer dissolved in a solvent. The material of the fibers may be insoluble or have a relatively low solubility in the solvent. In some embodiments, the coating may include an active agent. The fluid may include an active agent dissolved or dispersed in the fluid. In an embodiment, the material of the fiber may have a melting temperature greater than a melting temperature of the coating polymer. Additionally, all or a majority of the solvent may be removed from the applied fluid.

Furthermore, the fluid may be applied on the tube in a variety of ways known in the art. For example, the fluid may be sprayed on the tube or the tube may be dipped in the fluid. In one embodiment, the fiber layer may be disposed on a mandrel and then dipped in and/or sprayed with the fluid.

In one embodiment, the fiber layer may be disposed on a mandrel over a polymer layer including the coating polymer or another type of polymer previously formed on the mandrel. The previously formed polymer layer on the mandrel may be formed by dipping and/or spraying, as described above.

In some embodiments, after forming the coating, the tube or sheet may be heated to a temperature above the melting temperature of the coating polymer and below the melting temperature of the material of the fiber. The tube or sheet may then be cooled to a temperature below the melting temperature of the coating polymer such that a majority of the coating polymer in the formed tube or sheet is amorphous, crystalline, or partially crystalline.

In some embodiments, a method of fabricating a fiber-reinforced stent may include disposing a plurality of fibers within a mold for forming a structure. The structure may be, for example, a tube or a sheet. The fibers may be disposed within the mold in a number of ways. One embodiment may include disposing short fibers, as described above, in a random or substantially random fashion within the mold. In another embodiment, long fibers may be wound around a mandrel, disposed in the mold, in a helical or other fashion. In one embodiment, a woven structure, as described above, may be disposed in the mold.

Additionally, the method may further include disposing a matrix polymer that is partially or completely molten into the mold to at least partially embed the fibers within the molten polymer. In one embodiment, the fibers may include a material having a melting temperature greater than a melting temperature of the matrix polymer. The temperature of the molten polymer and the fibers within the mold may be less than a melting temperature of the material of the fiber.

In one embodiment, the matrix polymer may be a biostable or biodegradable polymer or a combination thereof. The material of the fibers may also be a biostable or biodegradable polymer or a combination thereof. In some embodiments, the material of the fibers may be a biostable and/or erodible metal. In an embodiment, the fibers may be combination of a polymeric and a metallic material. For example, the fibers may be a mixture of polymer and metallic particles.

The molten polymer may then be cooled to form the structure and a stent may be fabricated from the cooled structure. As indicated above, the polymer melt may be cooled in such a way to control the degree crystallinity of the matrix polymer.

A stent may be formed from a tube by forming a pattern in the tube including a plurality of interconnecting structural elements. As indicated above, a stent may be fabricated from a sheet by forming a tube from the sheet and forming a pattern in the tube including a plurality of interconnecting structural elements.

In one embodiment, a medicated stent may be fabricated by disposing an active agent into the mold. The active agent may be mixed or dispersed within the molten matrix polymer. Alternatively, the active agent may be mixed or dispersed with the fiber. In another embodiment, a coating including an active agent may be applied to the stent.

In further embodiments, a method of fabricating a fiber-reinforced stent may include disposing a plurality of fibers in an extruder for forming a structure. The structure may be, for example, a tube or a sheet. As described above, the fibers may be disposed within the extruder in a number of ways. One embodiment may include disposing short fibers, as described above, in a random or substantially random fashion within the extruder. In another embodiment, long fibers may be wound around a mandrel, disposed in the mold, in a helical or other fashion. In one embodiment, a woven structure, as described above, may be disposed in the extruder.

Additionally, the method may further include conveying a matrix polymer into the extruder. In one embodiment, the matrix polymer may have a melting temperature less than a melting temperature of a material of the fiber. In addition, the structure may then be formed with the extruder at a temperature greater than the melting temperature of the matrix polymer and less than the melting temperature of the material of the fiber. In an embodiment, at least some of the fibers may become embedded within matrix polymer.

In one embodiment, the matrix polymer may be a biostable or biodegradable polymer or a combination thereof. The material of the fibers may also be a biostable or biodegradable polymer or a combination thereof. In some embodiments, the material of the fibers may be a biostable and/or erodible metal. In an embodiment, the fibers may be combination of a polymeric and a metallic material. For example, the fibers may be a mixture of polymer and metallic particles.

The molten polymer may then be cooled to form the structure and a stent may be fabricated from the cooled structure. A stent may be fabricated from a tube or a stent as described above. As indicated above, the molten polymer melt may be cooled in such a way to control the degree crystallinity of the matrix polymer.

In some embodiments, a medicated stent may be fabricated by conveying an active agent into the extruder. In other embodiments, at least some of the fibers may include an active agent.

Figure 10:
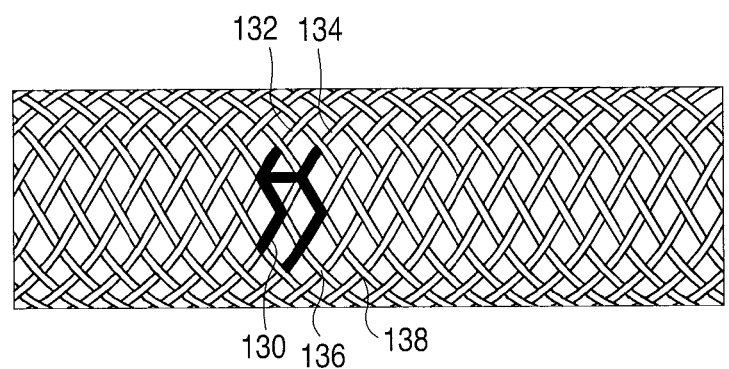
FIG. 10 depicts alignment of struts or structural elements with fibers.

As indicated above, a pattern including a plurality of interconnecting structural elements may be formed by laser cutting the pattern. In one embodiment, the pattern can be cut such that at least a portion of the structural elements may be aligned or substantially aligned with an orientation of at least some of the fibers. For example, FIG. 10 illustrates a pattern of struts or structural elements 130 that are aligned with the orientation of fiber segments 132, 134, 136, and 138.

In further embodiments, the circumferential strength and rigidity of a fiber reinforced stent may be enhanced by radial expansion of a tube. Polymer chain alignment in the continuous polymer phase may be induced along the circumferential direction to increase strength. In addition, radial expansion may also induce alignment of fibers in the tube, further enhancing circumferential strength.

The degree of polymer chain alignment induced with applied stress may depend upon the temperature of the polymer. For example, below the $T_g$ of a polymer, polymer segments may not have sufficient energy to move past one another. In general, polymer chain alignment may not be induced without sufficient segmental mobility. Above $T_g$, polymer chain alignment may be readily induced with applied stress since rotation of polymer chains, and hence segmental mobility, is possible. Between $T_g$ and the melting temperature of the polymer, $T_m$, rotational barriers exist. However, the barriers are not great enough to substantially prevent segmental mobility. As the temperature of a polymer is increased above $T_g$, the energy barriers to rotation decrease and segmental mobility of polymer chains tends to increase. Thus, as the temperature increases, polymer chain alignment is more easily induced with applied stress.

Rearrangement of polymer chains may take place when a polymer is stressed in an elastic region and in a plastic region of the polymer material. A polymer stressed beyond its elastic limit to a plastic region generally retains its stressed configuration and corresponding induced polymer chain alignment when stress is removed. The polymer chains may become oriented in the direction of the applied stress. The stressed polymer material may have a higher tensile strength and modulus in the direction of the applied stress.

Additionally, heating a polymer may facilitate deformation of a polymer under stress, and hence, modification of the mechanical properties of the polymer. A polymer deformed elastically with stress facilitated with heating may retain induced polymer chain alignment by cooling the polymer before relaxing to or towards an unstrained state.

In some embodiments, a polymer tube may be deformed at a temperature below the $T_g$ of the polymer of the continuous phase. Alternatively, it may be desirable to deform the tube in a temperature range greater than or equal to the $T_g$ of the continuous phase polymer and less than or equal to the $T_m$ of the polymer. As indicated above, a polymeric material deforms much more readily due to segmental motion of polymer chains above $T_g$. Deformation induces polymer chain alignment that may occur due to the segmental motion of the polymer chains. Therefore, heating the polymer tube prior to or contemporaneously with deformation may facilitate deformation particularly for polymers with a $T_g$ below an ambient temperature. Heating the tube contemporaneously with the deformation may be desirable since the deformation may occur at a constant or nearly constant temperature. Therefore, the induced polymer alignment and material properties may be constant or nearly constant.

In some embodiments, a fiber-reinforced polymer tube may be deformed radially by increasing a pressure in a polymer tube, for example, by conveying a fluid into the tube. Tension and/or torque may also be applied to the tube. The tube may be positioned in an annular member or mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube.

The polymer tube may also be heated prior to, during, and subsequent to the deformation. In general, it is desirable for the temperature during deformation to be greater than or equal to a glass transition temperature of the polymer and less than or equal to a melting temperature of the polymer. The polymer tube may be heated by the fluid and/or the mold.

Certain embodiments may include first sealing, blocking, or closing a polymer tube at a distal end. The end may be open in subsequent manufacturing steps. A fluid, (conventionally an inert gas such as air, nitrogen, oxygen, argon, etc.) may then be conveyed into a proximal end of the polymer tube to increase the pressure in the tube. The pressure of the fluid in the tube may act to deform the tube.

The increased pressure may deform the tube radially and/or axially. The fluid temperature and pressure may be used to control the degree of radial deformation by limiting deformation of the inside diameter of the tube as an alternative to or in combination with using the mold. In addition, it may be desirable to increase the pressure to less than about an ultimate stress of the continuous phase polymer to inhibit or prevent damage to the tube. The continuous phase polymer may be deformed plastically or elastically. As indicated above, a polymer elongated beyond its yield point tends to retain its expanded configuration, and hence, tends to retain the induced molecular orientation.

Additionally, the pressure inside the tube and the temperature of the tube may be maintained above ambient levels for a period of time to allow the polymer tube to be heat set. In one embodiment, the temperature of the deformed tube may be maintained at greater than or equal to the $T_g$ of the continuous phase polymer and less than or equal to the $T_m$ of the continuous polymer for a selected period to time. The selected period of time may be between about one minute and about two hours, or more narrowly, between about two minutes and about ten minutes. "Heat setting" refers to allowing polymer chains to equilibrate to different configurations in response to an elevated temperature. In this case, the polymer chains are allowed to adopt highly oriented structure at an elevated temperature. Polymer chain alignment is a time and temperature dependent process, therefore, a period of time may be necessary to allow polymer chains to realign at a given temperature that are stable in a deformed state of a polymeric material. Heat setting may also be facilitated by tension.

Further embodiments of the present invention relate to stents composed primarily or completely of polymeric fibers coiled or braided into a mesh tube or stent structure. A braided stent can provide sufficient radial strength, however, the radial profile of such a mesh, fiber structure can be higher than desirable. In particular, the "net points," which refer to the points of overlap of fibers, tend to increase the radial profile of a stent. Net points 142 are illustrated in FIG. 9. Embodiments of methods described herein allow fabrication of a fiber mesh stent with a sufficiently small profile and sufficiently high radial strength.

Certain embodiments of a method of fabricating a stent may include making a tube or stent structure from at least two types of fibers. In one embodiment, a first fiber may include a first polymer and a second fiber may include a second polymer.

Other embodiments of a method of fabricating a stent may include making a tube or stent structure from composite fibers including the first polymer and the second polymer. In some embodiments, the fibers of the tube may include an inner core including the first polymer and an outer layer or covering including the second polymer. In other embodiments, the outer covering may be the first polymer and the inner core may be the second polymer. In alternative embodiments, the fibers of the tube may be a mixture or blend of the first polymer and the second polymer.

In certain embodiments, the first polymer may have a softening temperature ($T_s$) lower than a softening temperature of the second polymer. Also, the first polymer may have a $T_m$ and a $T_g$ less than the $T_m$ and $T_g$ of the second polymer.

For example, in a stent including two different types of fibers, a first fiber may be made from poly (1-lactic acid) and a second fiber may be made from 10:90 poly(l-lactide-co-glycolide) (10% lactide, 90% glycolide). The poly (L-lactic acid) has a melting temperature of 175° C. and poly(l-lactide-co-glycolide) has a melting temperature of 200° C. Additionally, an exemplary composite fiber may be made from 50% poly (1-lactic acid) and 10:90 poly(l-lactide-co-glycolide).

Various embodiments of fabricating a stent having two types of fibers and/or fibers composed of a mixture of the first polymer and the second polymer may include heating the tube to a temperature range between a softening temperature of the first polymer and the melting temperature of the first polymer. In one embodiment, pressure is applied to the tube so as to flatten at least some of the fibers of the tube to reduce the radial profile of the tube. A heated fiber made of a first polymer may tend to flatten as pressure is applied, reducing the profile of the tube. Likewise, a heated fiber including the first polymer may also tend to flatten. In particular, the applied pressure may reduce the radial profile of the tube of at least some of the net points of the fibers.

In some embodiments, the second polymer may be adapted to provide high strength to the stent structure during heating, flattening of the fibers, and during use of the stent. In an embodiment, the temperature range may be below the $T_g$ of the second polymer. In this case, the second polymer may remain relatively rigid during heating a flattening of the first fiber. The temperature range may also be below the $T_s$ of the second polymer. Alternatively, the temperature range may be above the $T_s$ of the second polymer.

In some embodiments, a cross-section of a fiber may be circular. Alternatively, a cross-section of a fiber may have an oblong shape, for example, an oval or elliptical shape. Fibers with an oblong-shaped cross-section may allow greater surface coverage of a vessel, in addition to providing a smaller radial profile to the stent.

In one embodiment, the tube may be disposed over a mandrel during heating and flattening of the fibers. Pressure may be applied for flattening the fibers by a pressure tube disposed over the tube. In an alternate embodiment, the fibers may be heated and flattened in a heated crimper. Heat may be applied to the tube by a heated mandrel. The tube may also be heated by blowing a heated fluid onto the tube such as an inert gas, e.g., argon, air, oxygen, nitrogen, etc. Additionally, the tube may be allowed to heat set on the mandrel.

In an embodiment, the tube may be heated and the pressure applied at or near a fabricated diameter of the tube. The tube may be allowed to heat set by maintaining the tube in the temperature range for a selected period of time.

In some embodiments, the method may include radial expansion of the tube prior to, during, or subsequent to heating and/or applying pressure to flatten at least some of the fibers. As described above, radial expansion may induce molecular orientation in the fiber polymer that tends to increase the tensile strength of the fiber. In other embodiments, the tube may be crimped prior to, during, or subsequent to heating the tube and/or applying pressure to flatten at least some of the fibers.

Figure 11:
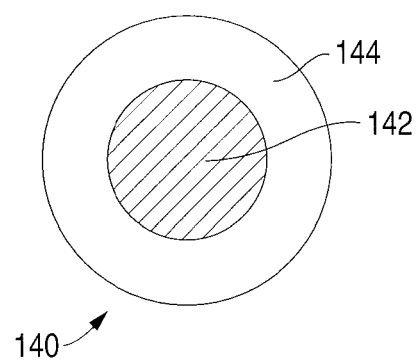
FIG. 11 depicts a radial cross-section of a composite fiber.
Figure 12:
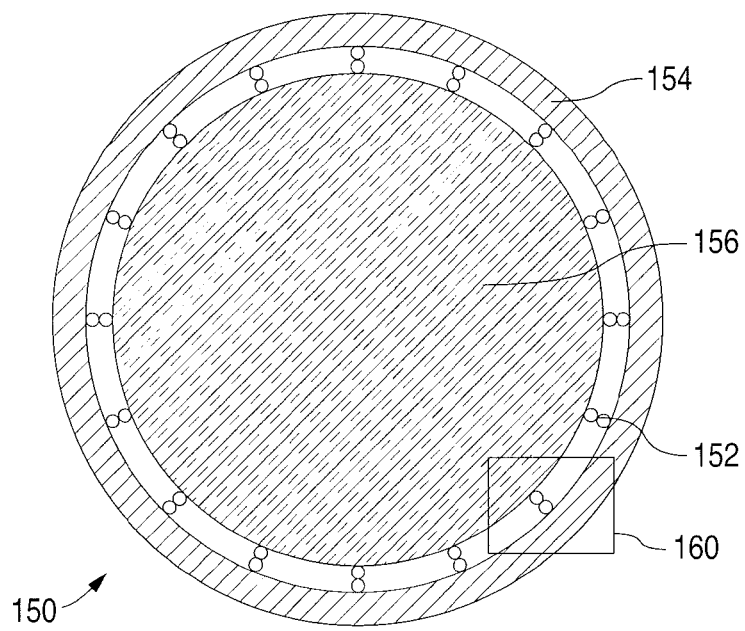
FIG. 12 depicts a radial cross-section of a system for heating and flattening fibers of a fiber stent.
Figure 13:
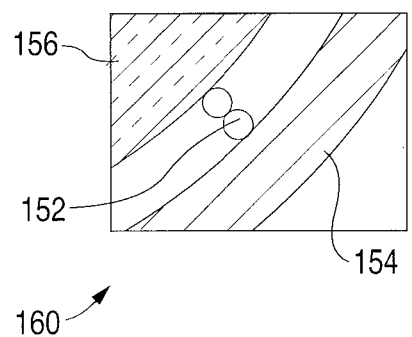
FIG. 13 depicts an expanded view of fibers in the system of FIG. 12 prior to flattening the fibers.
Figure 14:
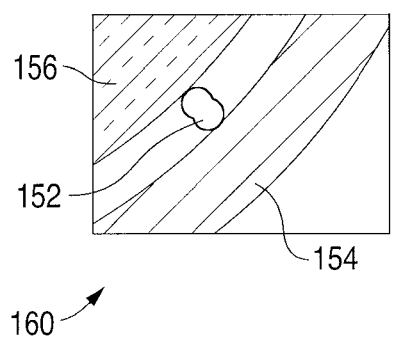
FIG. 14 depicts an expanded view of fibers in the system of FIG. 12 showing flattening of the fibers.

FIG. 11 depicts a radial cross-section of composite fiber 140. Fiber 140 has an inner core 142 of a first polymer and an outer layer 144 of a second polymer. FIG. 12 depicts a radial cross-section of a system 150 that can be used for heating and flattening fibers of a fiber stent. Overlapping fibers 152 are between a sliding wedge-type crimper 154 and a stationary mandrel 156. Wedge-type crimper 154 is heated and can apply pressure to the fibers of the stent. A region 160 including fibers 152, crimper 154, and mandrel 156 in FIG. 12 is shown in an expanded view in FIGS. 13 and 14. FIG. 13 illustrates fibers 152 prior to applying pressure to the fiber by inward movement of crimper 154 and FIG. 14 shows fibers 152 after applying pressure with crimper 154. FIG. 14 shows that fibers 152 have been flattened by crimper 154.

As indicated above, there are difficulties associated with manufacturing stents with small radiopaque markers. Various embodiments of stents and methods of making stents that include metallic films coupled and/or embedded within polymeric stents are disclosed herein. The metallic film may be sufficiently radiopaque to allow the stent to be visualized during use.

The stents may be formed by coupling and/or embedding metallic film in and/or on a polymeric tube. A stent may be fabricated by forming a pattern of interconnecting structural elements in the tube with the metallic film using, for example, a laser. Forming the pattern may include removal of some of the metallic film in or on the polymer in addition to removal of polymer.

In certain embodiments, the metallic film may include a biostable metal, a bioerodible metal, or a combination of a biostable and bioerodible metal. As indicated above, representative examples of bioerodible metals that may be used to fabricate an implantable medical device may include, but are not limited to, magnesium, zinc, and iron. Representative examples of biostable metals that may be used to fabricate an implantable medical device may include, but are not limited to, gold or platinum.

In certain embodiments, a stent may include metallic film coupled to a plurality of portions of a surface of the stent. Some embodiments of a method of making the stent may include coupling a metallic film to at least a portion of a surface of a polymeric tube. In one embodiment, the metallic film may include a band circumferentially aligned around a surface of the tube. A length of a band along a longitudinal axis of the stent may be less than or equal to the length of the tube. In another embodiment, the metallic film includes a longitudinal strip longitudinally aligned along the surface of the tube.

Figure 15:
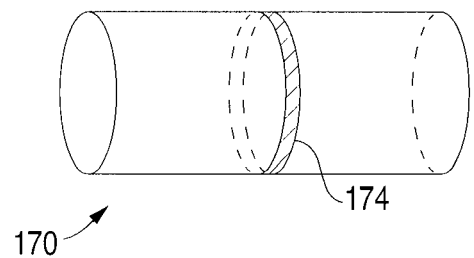
FIG. 15 depicts a polymeric tube with a circumferentially aligned metallic band coupled or adhered to the surface of the tube.
Figure 16:
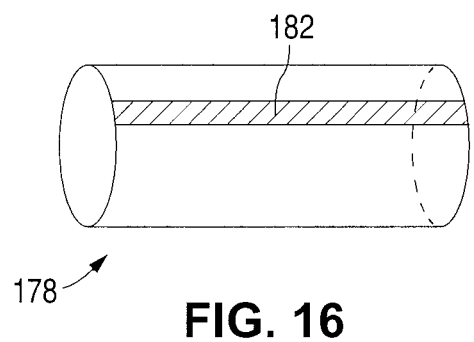
FIG. 16 depicts a polymeric tube with a longitudinally aligned strip of metallic film coupled or adhered to the surface of the tube.

As an illustration, FIG. 15 depicts a polymeric tube 170 with a circumferentially aligned metallic band 174 coupled or adhered to the surface of tube 170. In addition, FIG. 16 depicts a polymeric tube 178 with a longitudinally aligned strip of metallic film 182 coupled or adhered to the surface of tube 178.

In an alternate embodiment, a method of making a stent may include coupling the metallic film to at least a portion of a surface of a polymeric sheet. The sheet may then be rolled and bonded to form a tube.

Figure 17:
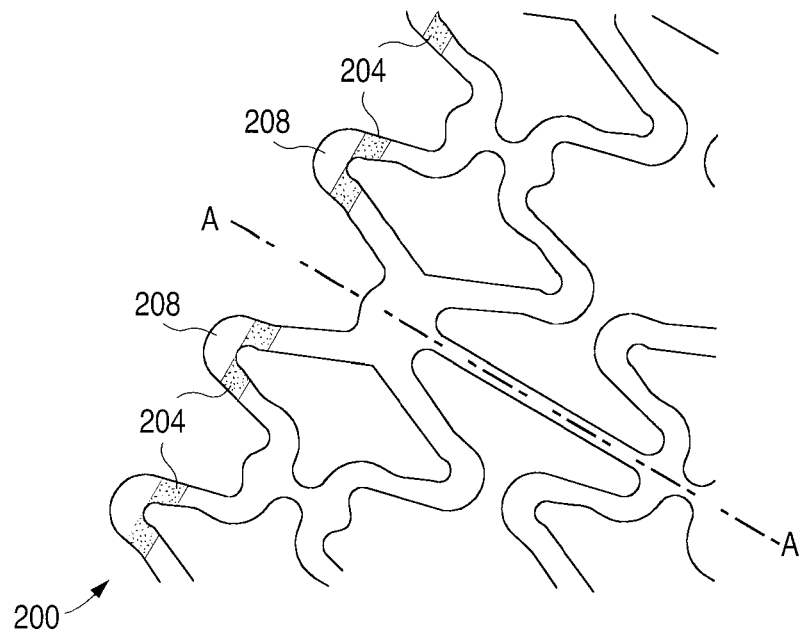
FIG. 17 depicts a stent with a circumferentially aligned metallic film on its surface.
Figure 18:
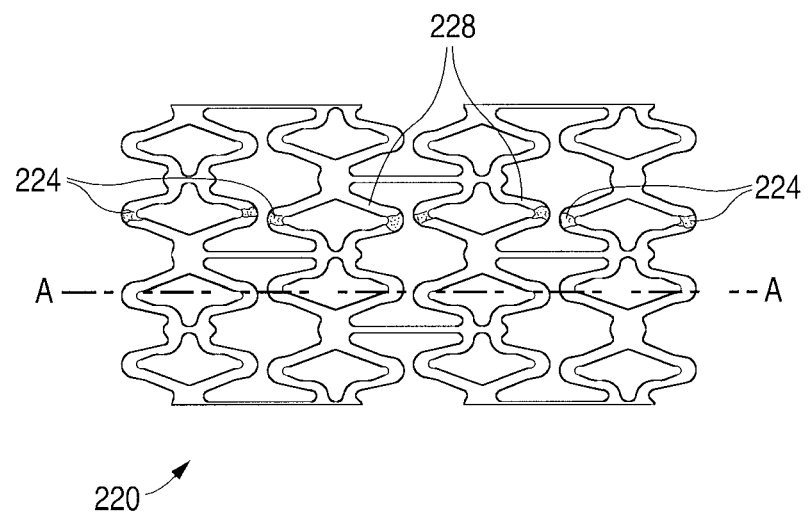
FIG. 18 depicts a stent with a longitudinally aligned metallic film on its surface.

FIG. 17 depicts a portion of a stent 200 fabricated from tube 170 in FIG. 15. Stent 200 has circumferentially aligned metallic film markers 204 coupled to structural elements 208. Line A-A corresponds to the longitudinal axis of the stent. FIG. 18 depicts a stent 220 fabricated from tube 178 in FIG. 16. Stent 220 has longitudinally aligned metallic markers 224 coupled to structural elements 228. Line A-A corresponds to the longitudinal axis of the stent.

In some embodiments, the metallic film may be coupled to the polymeric tube using any suitable biocompatible adhesive. In one embodiment, the adhesive may include a solvent. The solvent may dissolve the polymer of the polymeric tube to allow the metal film to be coupled to the tube. In another embodiment, the adhesive may include a solvent mixed with a polymer. The solvent or the solvent-polymer mixture may be applied to the tube followed by application of the metallic film. The solvent may then be removed by heating the tube, for example, in an oven.

Representative examples of solvents may include, but are not limited to, chloroform, acetone, chlorobenzene, ethyl acetate, 1,4-dioxane, ethylene dichloride, 2-ethyhexanol, and combinations thereof. Representative polymers may include biostable and biodegradable polymers disclosed herein that may be dissolved by the selected solvent.

In other embodiments, adhesives may include, but are not limited to, thermosets such as, for example, epoxies, polyesters and phenolics; thermoplastics such as, for example, polyamides, polyesters and ethyl vinyl acetate (EVA) copolymers; and elastomers such as, for example, natural rubber, styrene-isoprene-styrene block copolymers, and polyisobutylene. Other adhesives include, but are not limited to, proteins; cellulose; starch; poly(ethylene glycol); fibrin glue; and derivatives and combinations thereof.

Mixtures of solvents and another substance can be used to form adhesives. In some embodiments, mixtures of water and sugar such as, for example, mixtures of water and sucrose, can be used as an adhesive. In other embodiments, mixtures of PEG, or derivatives thereof, can be mixed with a suitable solvent to form an adhesive. Suitable solvents for PEG, or derivatives thereof, include, but are not limited to, water, ethanol, chloroform, acetone, and the like.

In other embodiments, the method may further include forming a coating above an outer surface of the stent with a metallic film coupled to a surface of the stent. The coating may be above at least a portion of the metallic film on the surface of the stent. In one embodiment, the coating may include a biostable or biodegradable polymer. In one embodiment, the coating may include an active agent or drug. The coating may be formed by applying a mixture of a polymer and a solvent, followed by removal of the solvent. In an embodiment, the polymer coating may inhibit or prevent detachment of the metallic film from the stent prior to substantial or complete biodegradation of a biodegradable coating.

Figure 19:
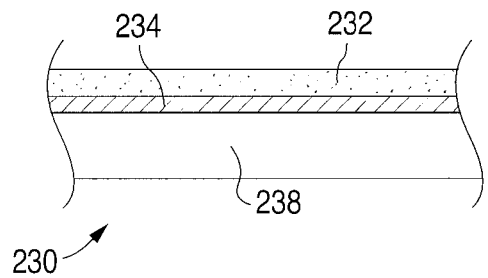
FIG. 19 depicts a cross-sectional view of a sidewall of a portion of a structural element of a stent with a coating above a metallic film on a polymeric substrate.

As an illustration, FIG. 19 depicts a cross-sectional view of a sidewall of a portion 230 of a structural element of a stent. A coating 232 is above a metallic film marker 234 which is coupled or adhered to a polymeric substrate 238. Coating 232 tends to inhibit detachment of marker 234 from substrate 238.

In other embodiments, structural elements of a stent may include two radial polymeric layers with metallic film embedded in a plurality of locations in between the layers. In certain embodiments, a method of making the stent may include forming a tube including a metallic film embedded between two polymer layers and fabricating a stent from the tube. In an embodiment, the metallic film may be a band circumferentially aligned around the tube in between the polymeric layers. In another embodiment, the metallic film may be a longitudinal strip longitudinally aligned along the tube in between the polymeric layers.

Alternatively, a sheet may be formed including the metallic film embedded between two polymer layers. The sheet may then be rolled and bonded to form a tube.

Figure 20:
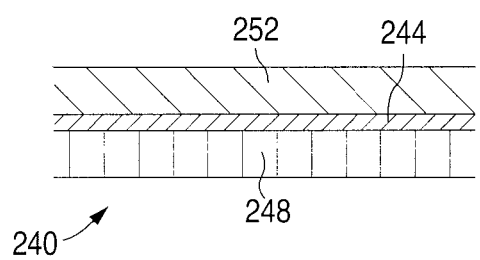
FIG. 20 depicts a cross-sectional view of a sidewall of a portion of a structural element of a stent with a metallic film embedded between an abluminal layer and a luminal layer.

As an illustration, FIG. 20 depicts a cross-sectional view of a sidewall of a portion 240 of a structural element of a stent. A metallic film marker 244 is embedded between a luminal polymeric layer 248 and an abluminal polymeric layer 252.

Some embodiments may include forming the tube by extruding an outer polymeric tubular layer over an inner tubular polymeric layer with a metallic film disposed above a surface of the inner layer. Extruding the outer layer over the inner layer may then embed the metallic film between the layers. In some embodiments, the melting temperature of an inner polymeric layer may be higher than the melting temperature of the outer layer. The outer layer may be extruded over the inner layer at a temperature above the melting temperature of the outer polymer layer and below the melting temperature of the inner polymer layer, allowing the inner layer to maintain its structural integrity.

In further embodiments, a method of making a stent may include elongating a polymeric tube so that a diameter of the stent decreases. A metallic film in the form of a metallic band may then be positioned around at least a portion of the elongated tube. The polymeric tube with the metallic band positioned around the tube may then be heated. In some embodiments, the method may further include allowing the heated tube to radially expand so as to couple the metallic band to the tube. The heated tube may radially expand to at least a diameter of the metallic band.

Representative examples of polymers that may be used to fabricate embodiments of implantable medical devices disclosed herein include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL™), poly(butyl methacrylate), poly(vinylidene fluoride-co-hexafluoropropene) (e.g., SOLEF® 21508, available from Solvay Solexis PVDF, Thorofare, N.J.), polyvinylidene fluoride (otherwise known as KYNAR®, available from Atofina Chemicals, Philadelphia, Pa.), ethylene-vinyl acetate copolymers, poly(vinyl acetate), styrene-isobutylene-styrene triblock copolymers, and polyethylene glycol.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:
heating a fiber mesh tube comprising a layer woven from two types of fibers, a first fiber comprising a first polymer and a second fiber comprising a second polymer, the first polymer having a Vicat softening temperature lower than a Vicat softening temperature of the second polymer, wherein the tube is heated to a temperature range between the Vicat softening temperature of the first polymer and the Vicat softening temperature of the second polymer, wherein the temperature range is below the melting temperature of the first polymer and the second polymer,
wherein the first polymer is a bioabsorbable polymer and the second polymer is a bioabsorbable polymer; and
applying pressure to the tube so as to flatten at least some of the fibers of the tube to reduce a radial profile of the tube.

2. The method of claim 1, wherein the tube is disposed over a mandrel during heating.

3. The method of claim 1, wherein pressure is applied with a heated crimper.

4. The method of claim 1, wherein the diameter of the tube is fixed during heating.

5. The method of claim 1, wherein the tube is heated and pressure applied at or near a fabricated diameter of the tube.

6. The method of claim 1, wherein the temperature of the tube is maintained in the temperature range for a selected period of time to allow heat setting of the tube.

7. The method of claim 1, further comprising radially expanding the tube prior to, during, or subsequent to heating and/or applying pressure to flatten at least some of the fibers.

8. The method of claim 1, wherein the first polymer has a lower melting temperature than the second polymer.

9. The method of claim 1, wherein the temperature range is below the glass transition temperature ($T_g$) of the second polymer.

10. The method of claim 1, wherein the applied pressure reduces a radial profile of at least some of the net points of the fibers.

11. A method of making a stent comprising:
heating a fiber mesh tube comprising a layer woven from two types of fibers, a first fiber comprising a first polymer and a second fiber comprising a second polymer, the first polymer having a Vicat softening temperature lower than a Vicat softening temperature of the second polymer, wherein the tube is heated to a temperature range between the Vicat softening temperature of the first polymer and the Vicat softening temperature of the second polymer, wherein the temperature range is below the melting temperature of the first polymer and the second polymer, wherein the first polymer is a bioabsorbable polymer and the second polymer is a bioabsorbable polymer;

radially expanding the tube during the heating; and applying pressure to the tube so as to flatten at least some of the fibers of the tube to reduce a radial profile of the tube.

12. The method of claim 11, wherein the temperature range is less than the $T_g$ of the second polymer.

* * * * *